(12) United States Patent
Satoh et al.

(10) Patent No.: US 8,460,861 B2
(45) Date of Patent: Jun. 11, 2013

(54) METHOD FOR PRODUCING HYDROGEN-CONTAINING FLUID ABLE TO BE USED IN A LIVING ORGANISM

(75) Inventors: Bunpei Satoh, Kanagawa (JP); Kazuyoshi Arai, Kanagawa (JP); Fumitake Satoh, Kanagawa (JP)

(73) Assignee: MIZ Co. Ltd., Kanagawa (JP)

( * ) Notice: Subject to any disclaimer, the term of this patent is extended or adjusted under 35 U.S.C. 154(b) by 78 days.

(21) Appl. No.: 12/939,630

(22) Filed: Nov. 4, 2010

(65) Prior Publication Data

US 2011/0111048 A1      May 12, 2011

Related U.S. Application Data

(63) Continuation of application No. PCT/JP2010/052201, filed on Feb. 15, 2010.

(30) Foreign Application Priority Data

| Mar. 13, 2009 | (JP) | 2009-061785 |
| Mar. 19, 2009 | (JP) | 2009-068434 |
| Sep. 25, 2009 | (JP) | 2009-221567 |

(51) Int. Cl.
 *A01N 1/02* (2006.01)

(52) U.S. Cl.
USPC ............... 435/2; 424/600; 210/634

(58) Field of Classification Search
None
See application file for complete search history.

(56) References Cited

FOREIGN PATENT DOCUMENTS

| JP | 63-028370 A | 2/1988 |
| JP | 08-056632 A | 3/1996 |
| JP | 2002-301483 A | 10/2002 |
| JP | 2005-126384 A | 5/2005 |

*Primary Examiner* — Sandra Saucier
(74) *Attorney, Agent, or Firm* — Muncy, Geissler, Olds & Lowe, PLLC

(57) ABSTRACT

A producing method for a living organism-applicable hydrogen-contained fluid, which includes hydrogen molecules in living organism-applicable fluid enclosed in a container (2*i*) with hydrogen molecule permeability, is provided. This method includes a hydrogen exposing step of exposing hydrogen molecules to the container (2*i*) in which the living organism-applicable fluid is enclosed from the outside of the container without opening the container. The container with hydrogen molecule permeability is one that allows a dissolved hydrogen concentration of a normal saline solution to be 1 ppb or greater when the container filled with the normal saline solution is immersed for 5 hours in a volume of hydrogen water, which stably maintains an approximately saturated state (1.6 ppm at 20 C degrees under 1 barometric pressure) and is 20 times the content volume of the container.

14 Claims, 7 Drawing Sheets

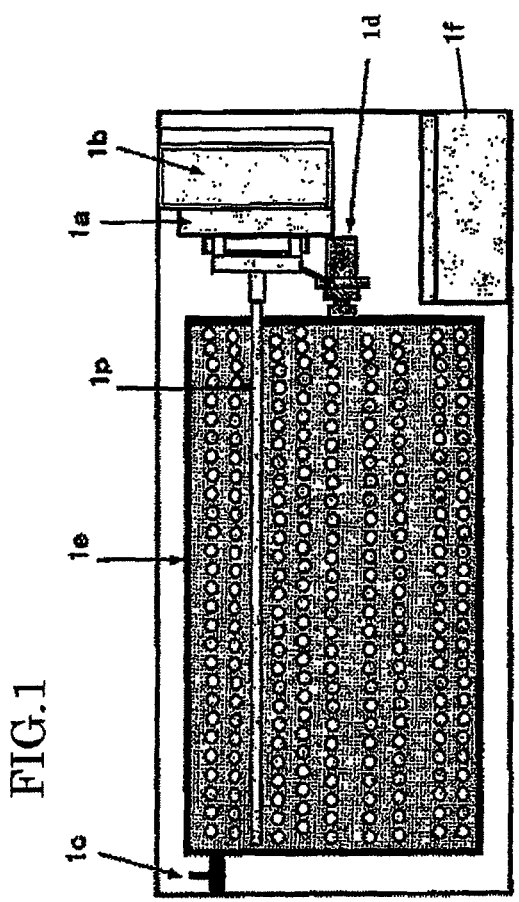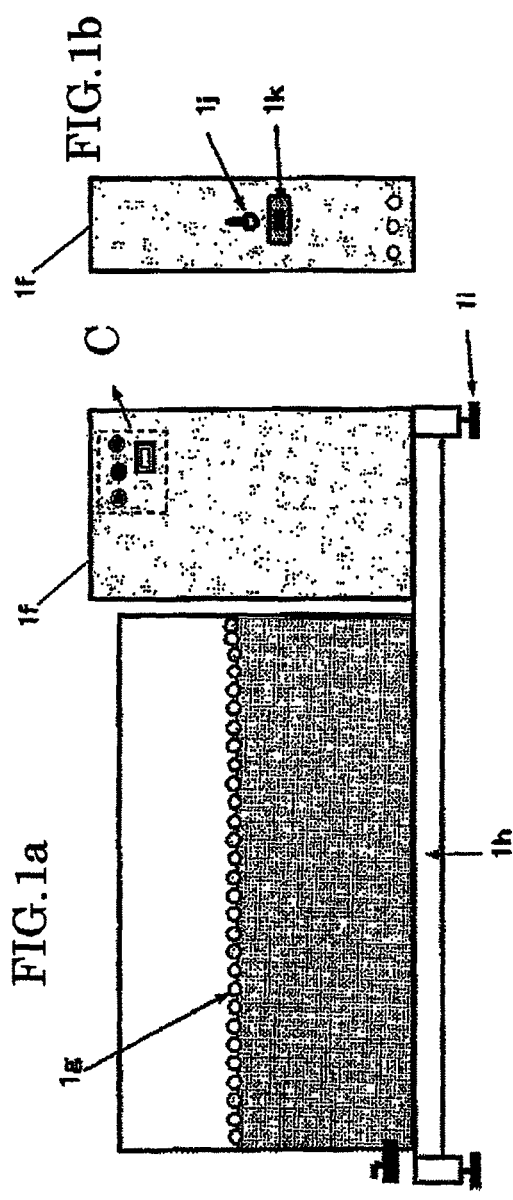

METHOD FOR PRODUCING HYDROGEN-CONTAINING FLUID ABLE TO BE USED IN A LIVING ORGANISM

BACKGROUND OF THE INVENTION

1. Technical Field of the Invention

The present invention relates to a producing method for living organism-applicable hydrogen-contained fluid and a producing apparatus for the same.

It is to be noted that the contents described and/or illustrated in the documents relevant to Japanese Patent Application No. 2009-061785 filed on Mar. 13, 2009, No. 2009-068434 filed on Mar. 19, 2009, No. 2009-221567 filed on Sep. 25, 2009, and PCT Application No. PCT/JP2010/052201 filed on Feb. 15, 2010, will be incorporated herein by reference, as a part of the description and/or drawings of the present application.

2. Description of the Related Art

Inhalation of hydrogen gas, drinking of hydrogen water, injection of living organism-applicable hydrogen-contained fluid, and the like are well-known as means of transferring hydrogen molecules as a substance for medical use into a living organism (Japanese Unexamined Patent Application Publication No 2005-126384). Injection of a living organism-applicable hydrogen-contained fluid is considered as an ideal transfer means since there are no handling risks such as in the case of inhaling hydrogen gas.

However, the living organism-applicable hydrogen-contained fluid administered to a living organism for the purpose of maintaining vital functions and prevention or treatment of diseases and disorders requires strict fluid quality management from the viewpoint of guarantee of physical and chemical purity and countermeasures against bacteria and microorganisms. As a result, there is a problem that if the producing process is completed and the container in which the living organism-applicable fluid is enclosed is opened, fluid quality guarantee cannot be secured. Therefore, means for pouring hydrogen from the outside into the container without opening the container is desirable.

SUMMARY OF THE INVENTION

The objective of the present invention is to provide a producing method for producing a living organism-applicable hydrogen-contained fluid to be used for injection, intravenous drip, transfusion, organ preservation, and the like without opening the container in which the living organism-applicable fluid is enclosed, and a producing apparatus for the same.

The present invention solves the aforementioned problem by exposing to a gas or liquid including hydrogen the outer surface of the container with hydrogen molecule permeability, in which the living organism-applicable fluid to be used for injection, intravenous drip, transfusion, organ preservation, and the like is enclosed.

According to the present invention, hydrogen can be easily included in the living organism-applicable fluid without changing already existing producing processes.

BRIEF DESCRIPTION OF DRAWINGS

FIG. 1 shows a top view of a producing apparatus for a living organism-applicable hydrogen-contained fluid according to an embodiment of the present invention;

FIG. 1a is a side view of the producing apparatus of FIG. 1;

FIG. 1b is a front view of the control box of the producing apparatus of FIG. 1;

FIG. 1c is an enlarged view from FIG. 1 showing an enlarged view of the dotted line portion referenced by C;

DESCRIPTION OF THE PREFERRED EMBODIMENT

Figure 2:
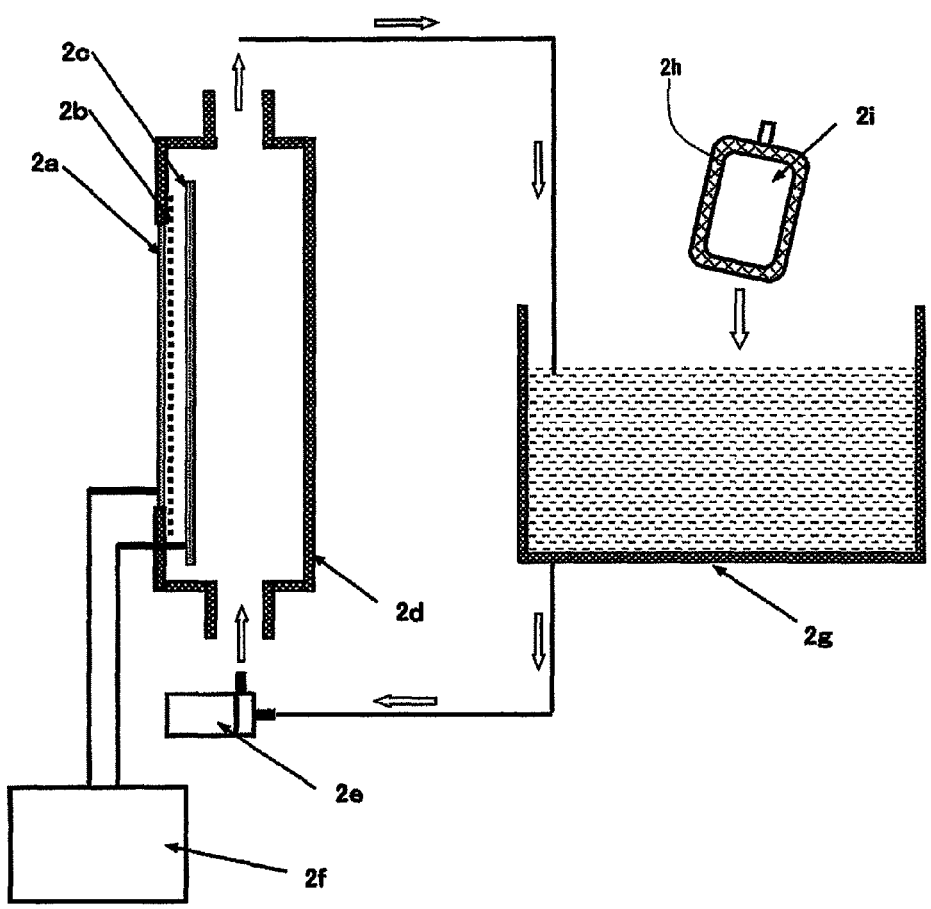
FIG. 2 is a block diagram conceptually showing the producing apparatus for a living organism-applicable hydrogen-contained fluid of FIG. 1.

Embodiments according to the present invention are described below. FIGS. 1 to 7 are diagrams showing a producing apparatus for living organism-applicable hydrogen-contained fluid according to embodiments of the present invention; FIGS. 1, 1a, 1b, 1c and are diagrams showing a first embodiment, and FIGS. 3 to 7 are each a diagram showing producing apparatus for living organism-applicable hydrogen-contained fluid according to another embodiment.

In FIG. 1, reference numeral 1a is electrolysis unit, 1b is a tray, 1c is a drain cock, 1d is a circulation pump, 1e is a hydrogen storage container and 1f is a control box. The front of the producing apparatus of FIG. 1 is shown in FIG. 1b wherein the adjuster 1j and the inlet (power supply input) 1k are shown. In the side view of the producing apparatus shown in FIG. 1a, the float 1g for hydrogen diffusion prevention is shown. Also, the platform 1h for the producing apparatus with its adjuster 1i can be seen. In the enlarged view of FIG. 1c, the power indicating lamp 1l, the operation indicating lamp 1m the electrolyzing indicating lamp 1n and the operation start switch 1o are shown. In FIG. 1, a flush hose 1p extends over the hydrogen storage container 1e.

For example, to describe the example shown in FIG. 2, the producing apparatus of this example accommodates a container 2i, such as an infusion solution (intravenous drip) bag, of living organism-applicable fluid in a separate container 2g suitably large enough to accommodate the container of the living organism-applicable fluid, and supplies a liquid or a gas containing hydrogen molecules to the container 2g (hereafter referred to as hydrogen storage container). While the living organism-applicable fluid and the hydrogen molecules within the hydrogen storage container 2g are separated from each other by the container 2i of the living organism-applicable fluid within the hydrogen storage container 2g, over time, the hydrogen molecules within the hydrogen storage container 2g gradually permeate into the living organism-applicable fluid. An electrolytic cell housing 2d is connected to the hydrogen storage container 2g. A circulation pump 2e is provided. Within the electrolytic cell housing 2d, an anode plate 2a, cation-exchange membrane 2b and cathode plate 2c are provided. A power unit 2f supplies power. A gas permeable film 2h is provided.

While plastic containers made of a material, such as polyethylene, polypropylene, and polystyrene, used for the aforementioned infusion solution bag and intravenous bag are suitable for the container 2g (FIG. 2) for the living organism-applicable fluid, it is not limited thereto as long as is a container (membrane) through which hydrogen can permeate. Even if it is a container with an oxygen gas barrier characteristic and moisture barrier characteristic, hydrogen molecules, which are the smallest molecules, can most often permeate without difficulty. Note that while the container for the living organism-applicable fluid allows absorption and separation of hydrogen so as to penetrate therethrough (preferably selectively penetrate), it is further preferable if processing for irreversibly controlling the penetration direction of the hydrogen such that the hydrogen that has penetrated through to be included in the living organism-applicable fluid is stably kept within the fluid is carried. Moreover, in order to confirm amount of consumption of the living organism-applicable fluid during drip infusion or the like, use of a transparent or semi-transparent container allowing external confirmation of water level of the content is preferred.

Note that the present invention, which can make hydrogen molecules be included in ready-made living organism-applicable fluid from the outside of the container, is characteristic of making the hydrogen molecules be included therein without changing anything to the content of the container (nondestructively (without opening it)). In other words, the present invention is characteristic of basically being used for a container that is either closed to the outside (or sealed up) and opened for the first time at the time of use, or even if it is opened once, it is closed at the time of implementing the present invention.

Furthermore, by freezing the living organism-applicable fluid including the hydrogen molecules, container and all, leakage of the hydrogen molecules from the container can be prevented. Taking leakage of the hydrogen molecules during the freezing process into consideration, the shortest possible freezing period is preferred. More specifically, it is preferable that at least 80% of living organism-applicable hydrogen-contained fluid can be frozen within 10 hours, more preferably within 5 hours, even more preferably within 3 hours, even more preferably within 1 hour, and even more preferably within 0.5 hour. In addition, it is preferable that the dissolved hydrogen concentration in the living organism-applicable hydrogen-contained fluid immediately after a part or all thereof has been thawed after 24 hours have elapsed is kept at 0.05 ppm or greater, more preferably 0.1 ppm or greater, even more preferably 0.2 ppm or greater, even more preferably 0.3 ppm or greater, even more preferably 0.4 ppm or greater, even more preferably 0.5 ppm or greater, even more preferably 0.6 ppm or greater, even more preferably 0.7 ppm or greater, even more preferably 0.8 ppm or greater, even more preferably 0.9 ppm or greater, and even more preferably 1.0 ppm or greater.

In general, the 'hydrogen storage container' and the 'container for the living organism-applicable fluid' according to the present invention can be categorized according to high and low hydrogen permeability of the storage container or container. It can be said that a container that has not-so-high hydrogen permeability is appropriate as the hydrogen storage container, and a container that has high hydrogen permeability is appropriate as the container for the living organism-applicable fluid. However, strictly speaking, since hydrogen molecules, which are the smallest molecules, permeate gradually through most containers over time as described above, containers that have medium to high hydrogen permeability are appropriate as the container for the living organism-applicable fluid according to the present invention. Here, it can be said that a container that has medium hydrogen permeability is one that, when the container filled or almost filled with physiological saline solution is immersed for 5 hours in a volume of hydrogen dissolved water twenty times that of the container volume stably keeping at almost a saturated concentration (1.6 ppm at a water temperature of 20 C degrees under 1 barometric pressure), has a dissolved hydrogen concentration in the physiological saline solution 1 ppb or greater, preferably 10 ppb or greater, or most preferably 100 ppb or greater and less than 0.8 ppm. If the container for the living organism-applicable fluid has hydrogen permeability of medium degree or greater, the living organism-applicable fluid can reach a desired hydrogen dissolved concentration using the present invention after a specified period of time. Moreover, it can be said that the container that has high hydrogen permeability is one that, when the container filled with physiological saline solution is immersed for 5 hours, has a dissolved hydrogen concentration in the physiological saline solution of 0.8 ppm or greater. Furthermore, it can be said that the container that has low hydrogen permeability is one that, when the container filled with physiological saline solution is immersed for 5 hours, has a dissolved hydrogen concentration in the physiological saline solution of less than 100 ppb, preferably less than 10 ppb, and more preferably less than 1 ppb.

Living organism-applicable fluid is a concept indicating in general fluids applied orally or parenterally to living organisms for improvement in maintaining vital functions and prevention, treatment, and the like of diseases and disorders; those fluids include normal saline solution prepared in terms of osmolality for use as injection, intravenous drip, transfusion, and the like, liquid for injection for resupply of liquids, nutrition, and electrolytes, oral liquid, liquid for injection in which a medical agent (including an anticancer agent and a vasodilator such as prostaglandin) is dissolved, physiologic saline solution, a liquid medical agent, blood preparation (blood for blood transfusion) and own blood to be used for blood transfusion, enteral solution, organ preservative solution prepared to preserve organs, living organism-applicable fluid including lymph cells and vaccines used in cancer immune therapy, vaccine therapy, and similar therapies, peritoneal dialysis solution, dialysis solution, myocardial protective medicine, and the like. Moreover, in this specification, the term 'living organism-applicable fluid' can also indicate biological fluid or biological water of the living organism itself. Note that in the case of injecting living organism-applicable fluid, after subjecting the living organism-applicable fluid to nondestructive hydrogen-including processing according to the present invention using a hydrogen-permeable container such as an infusion solution bag, puncturing the bag mouth with a hypodermic syringe, sucking up a necessary amount into the syringe, and using it can be carried out.

The hydrogen storage container indicates those in general that are capable of keeping for a given length of time hydrogen supplied into the container from the outside, or hydrogen supplied into the container through means provided by the storage container itself. While it is possible to supply hydrogen in consideration for reduced portion of hydrogen, basically, a container having relatively low gas permeability is desired in order to maintain the supplied hydrogen for a long period of time. Similarly, in order to prevent the hydrogen supplied to the container from dissipating into the air, a design allowing closure or seal-up of the container as needed using an opening and closing upper lid is desired. Moreover, in order to heighten transmission or permeation efficiency into the living organism-applicable hydrogen fluid, provision of a pressure (pressure regulation) device, a cooling (temperature regulation) device, a hydrogen concentration regulation device (or instructions for hydrogen concentration regulation), and an immersion/exposure time regulation device (or instructions for immersion/exposure time regulation) is desired. Note that in the case of applying pressure to the hydrogen storage container, barometric pressure of 1.0 or greater, preferably 1.2 or greater, more preferably 1.5 or greater, and most preferably 2.0 or greater is desired.

Such hydrogen storage container is not limited by container size, and the room itself into which the hydrogen molecules are supplied can be considered a hydrogen storage container, as are recompressing locks generally used in treatment for decompression disease.

While liquid containing hydrogen molecules such as 'hydrogen-contained water', gas containing hydrogen molecules such as 'hydrogen-contained gas', and solid containing hydrogen molecules such as a hydrogen stored alloy are examples of a carrier for hydrogen to be supplied to the hydrogen storage container, it is not limited thereto, and does not exclude other possible intermediate phases such as liquid crystal. Note that in this specification, it may simply be written as 'hydrogen-contained water' regardless of the intention of the inventor(s) indicating a 'liquid containing hydrogen molecules'. However, since the liquid carrier for including hydrogen according to the present invention is not limited to only water, 'hydrogen-contained water' should be reread as 'liquid containing hydrogen molecules' or 'hydrogen-contained liquid' according to the context.

In this case, while 'hydrogen-contained water' is produced through means of bubbling hydrogen gas into water, dissolving the hydrogen gas in the water under pressure, decomposing the water by an electric current, generating hydrogen in the water through a chemical reaction (for example, a hydrogen generating reaction between water and a metal with higher ionization tendency, such as magnesium or zinc, than hydrogen), and/or similar steps, it is not limited thereto. The dissolved hydrogen concentration in the hydrogen-contained water should be the greater amount than the living organism-applicable fluid to which hydrogen is to be included; however, taking work efficiency into consideration, 0.01 mg/L or greater, preferably 0.05 mg/L, more preferably 0.1 mg/L, even more preferably 1.0 mg/L, even more preferably a saturated concentration, and even more preferably a stable saturated concentration (maintain nearly saturated concentration for at least 3 hours or more) at a water temperature of 20 C degrees under 1 barometric pressure is desired. Note that such hydrogen-contained fluid has a merit in that it is easier to handle than the hydrogen-contained gas described later requiring concern for safety.

Moreover, in order to expose the container of the living organism-applicable fluid to hydrogen of a stably high concentration (0.05 mg/L or greater), it is desirable for the hydrogen storage container to either include a device for supplying hydrogen gas to liquid such as water to be provided in the container, or an electrolyzed water generating device that can continuously electrolyze liquid such as water supplied into the container (or the hydrogen storage container itself is a part (cathode chamber) of such electrolyzed water generating device). According to the embodiment shown in FIG. 2, this can be implemented by circulating the hydrogen-contained water, which has been generated in a cathode chamber in an electrolytic cell housing 2d, into the hydrogen storage container 2g. Alternatively, according to the embodiments shown in FIG. 3 and FIG. 4, cathode chambers in electrolytic cell housings 3d and 4d, respectively, each constitute a hydrogen storage container itself.

Figure 3:
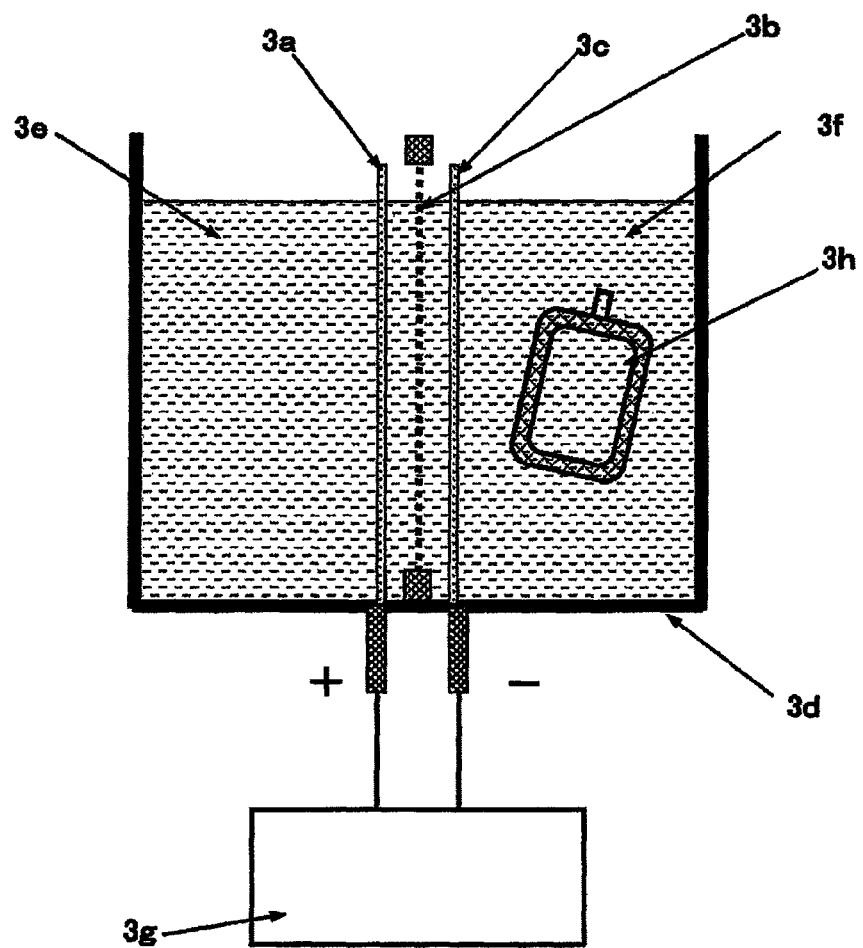
FIG. 3 is a block diagram conceptually showing a producing apparatus for a living organism-applicable hydrogen-contained fluid according to another embodiment of the present invention.
Figure 4:
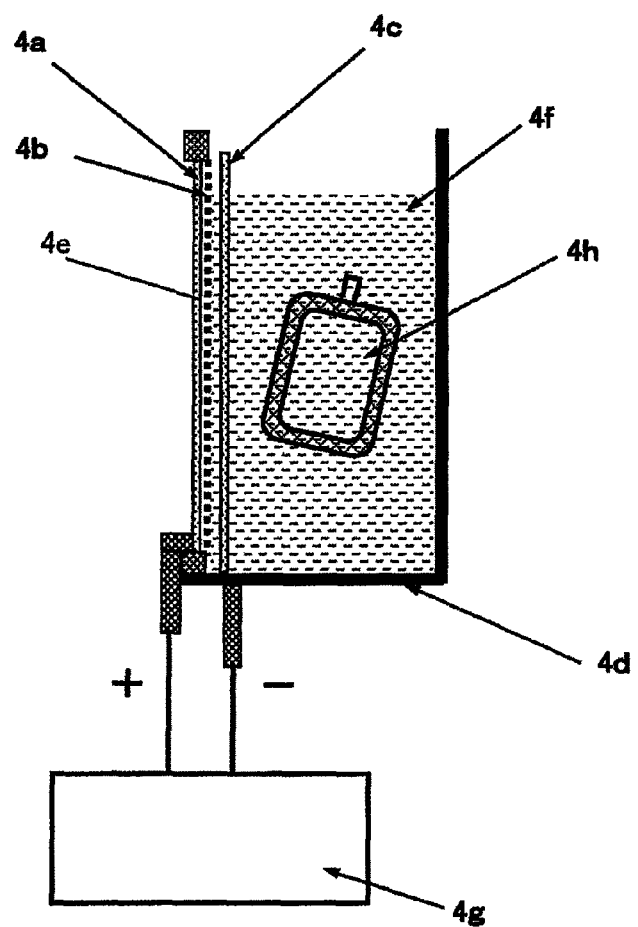
FIG. 4 is a block diagram conceptually showing a producing apparatus for a living organism-applicable hydrogen-contained fluid according to yet another embodiment of the present invention.

In particular, in FIG. 3, a double-cell type electrolysis device is provided. An intravenous drip bag 3h is in the electrolytic cell housing 3d. An anode plate 3a, membrane 3b and cathode plate 3c are provided in electrolytic cell housing 3d. An anode chamber 3e and a cathode chamber 3f are provided. The power unit 3g is connected to the anode plate 3a and the cathode plate 3c. FIG. 4 shows an anode membrane adhesive type single-cell type electrolysis device. The electrolytic cell housing 4d with an anode plate 4a, membrane 4b and cathode plate 4c of another embodiment of the present invention. The anode chamber 4e is provided as tiny space between 4a and 4b. The intravenous drip bag 4h is in the cathode chamber 4f.

Moreover, it is also desirable for the hydrogen storage container to include a device for maintaining and managing the hydrogen gas concentration or dissolved hydrogen concentration in the hydrogen storage container within a fixed range. As an example, a device characterized by starting (restarting) electrolysis or supplying (resupplying) hydrogen gas when the hydrogen gas concentration or dissolved hydrogen concentration in the hydrogen storage container drops below a constant value based on a dissolved hydrogen measuring device and measurement signal thereof can be considered.

Furthermore, it is also desirable for the hydrogen storage container to include a device for controlling the immersion period of the living organism-applicable fluid. As an example, a device characterized by setting a timer in accordance with a target value of dissolved hydrogen to be included in the living organism-applicable fluid and/or characteristics (material, thickness, hydrogen permeability, or the like) of the container of the living organism-applicable fluid can be considered.

Furthermore, it is desirable for the hydrogen storage container to include a device for nondestructively monitoring the dissolved hydrogen concentration of the living organism-applicable fluid using a laser beam, infrared light, or the like without taking a sample of the living organism-applicable fluid.

Furthermore, it is desirable for the hydrogen storage container to include a device for controlling the temperature or liquid temperature in the hydrogen storage container.

Even in order to expect sufficiently effective results for the living organism, it is desired that dissolved hydrogen (referred to as DH hereafter) concentration in the living organism-applicable hydrogen-contained fluid is 0.01 mg/L or greater, preferably 0.05 mg/L, more preferably 0.1 mg/L, even more preferably 0.2 mg/L or greater, even more preferably 0.4 mg/L or greater, even more preferably 0.6 mg/L or greater, even more preferably 0.8 mg/L or greater, and even more preferably 1.0 mg/L or greater at a temperature of 20 C degrees under 1 barometric pressure at the time of manufacture.

Diseases and disorders that can be in the applicable region of the living organism-applicable hydrogen-contained fluid include circulatory system diseases, such as arteriosclerosis, ischemic reperfusion disorder, and liver damage due to chemicals or harmful substances, digestive system diseases, such as gastric ulcer and gastric mucosal disorder, respiratory diseases, complications from diabetes (e.g., high blood pressure, stroke, heart attack), renal diseases, cataract, skin diseases, various inflammatory diseases, neurological disorders, cancer, and oxidant stress diseases attributable to free radicals and lipid peroxide such as aging, and while it is particularly applicable to diseases related to acute oxidant stress such as ischemic reperfusion disorder, it is not limited thereto.

Moreover, while much of the side effects of cancer treatments are attributed to active oxygen, treatment can be accomplished while reducing side effects by administering the living organism-applicable hydrogen-contained fluid (or hydrogen-contained anticancer agent) to the patient during, before, or after cancer treatment.

Note that minimal amount of a catalyst such as a precious metal colloid (platinum, palladium, or a similar metal) can be added as needed to the living organism-applicable fluid in order to heighten reactivity of the hydrogen molecules.

The present invention is characterized in that hydrogen molecules are nondestructively included in a closed container of the living organism-applicable fluid, where the container has hydrogen permeability, by exposing hydrogen molecules thereto from the outside of the container so that a new effectiveness is added to the primary ones of the already existing living organism-applicable fluid.

Until now, regardless that the method of including hydrogen gas from the air in ultrapure water via a hydrogen-permeable film has been well-known in technical fields such as surface washing of semiconductor bases, a method of including hydrogen molecules in living organism-applicable fluid by exposing a closed, hydrogen-permeable container filled with the living organism-applicable fluid to hydrogen gas from the outside of the container has not yet been considered. This is because the hydrogen-permeable container means that it is easy for hydrogen to enter and exit, and it is thus self-evident that requests that living organism-applicable "hydrogen"-contained fluid housed in a "hydrogen" permeable container has its active element stably retained for at least the effective period of a product, and a given quantity of the active element is sent to a living organism (including humans and animals such as dogs, cats, or racehorses) at the time of use cannot be fulfilled.

According to facts and observation by the inventor(s), the living organism-applicable hydrogen-contained fluid reduces the molecular hydrogen or active element at a rate of at least 20 to 30% during one hour, although it does fluctuate due to material and thickness of the container, contact area to air, and the like. In other words, for example, even if the living organism-applicable fluid has up to a saturation concentration (1.6 ppm at 20 C degrees under 1 barometric pressure) of molecular hydrogen included therein, it is calculated that after 24 hours, only approximately 0.0004 . . . ppm to 0.009 . . . ppm or $1/3654$ to $1/169$ thereof will be left. In addition, it is naturally judged that any forms of pharmaceuticals that lose their active elements at this reduction rate cannot be provided for actual use.

Even if it is a container through which hydrogen is transmitted, as long as hydrogen molecules are included in the living organism-applicable fluid at the time of use at a medical site or similar site presuming reduction in hydrogen beforehand, it is possible to administer the active element even while it continues to reduce. Consequently, the present invention is based on the inventor's idea that it is possible, according to the fact that hydrogen is permeable, to change "a demerit that hydrogen molecules or active element is lost" to "a merit that hydrogen molecules can be included in commercially available living organism-applicable fluid without being invasive at all to the living organism-applicable fluid that is guaranteed of sterilization and physical and chemical purity".

To elaborate even further, the idea of the inventor(s) has extended to such a degree that if the nondestructive hydrogen inclusion method according to the present invention is used in a subsequent process to completion of packaging the product at not only a medical site but even at a producing facility of living organism-applicable fluid, for example, a new function derived from the hydrogen molecules can be added to the primary effectiveness and functions of all the living organism-applicable fluids already sold on the market. Reduction in hydrogen molecules in a distribution process once the product is shipped can be resolved through resourcefulness such as freezing the product and then shipping it, as described above, or as described later, covering the container of the living organism-applicable fluid with a hydrogen less-permeable external bag.

More specifically, according to the present invention, hydrogen can be easily included in the living organism-applicable fluid without changing the already existing producing processes. In other words, without changing the content (living organism-applicable fluid) produced under strict management based on standards such as pharmaceutical codex, new effectiveness can be added to primary effectiveness of the content just by sending a minimal amount (several micrograms to several milligrams per liter) of hydrogen or a safe gas for the living organism into the container from outside.

Moreover, in the case of preparing living organism-applicable hydrogen-contained fluid at the time of use at a medical site, consumption of hydrogen during the distribution process or storage period is not a problem.

Furthermore, the present invention can be used for the purpose of supplementing hydrogen molecules to living organism-applicable fluid that already includes hydrogen molecules.

WORKING EXAMPLES

Working examples according to the present invention are described below. Note that when there is no particular explanation in this specification, various gauges used for measuring various physicality values are as follows: pH meter (including temperature indicator) manufactured by Horiba, Ltd. (main body type: D-13, probe type: 9620-10D); ORP meter manufactured by Horiba, Ltd. (main body type: D-25, probe type: 9300-10D); EC meter manufactured by Horiba, Ltd. (main body type: D-24, probe type: 9382-10D); DO meter manufactured by Horiba, Ltd. (main body type: D-2•5, probe type: 9520-10D); and DH meter (dissolved hydrogen meter) manufactured by DKK-Toa Corporation (main body type: DHDI-1, electrode (probe) type: HE-5321, transponder: DHM-F2).

Working Example 1

Commercially available normal saline solution ('Japanese Pharmacopoeia normal saline solution, Otsuka normal saline' produced by Otsuka Pharmaceutical Co., Ltd.) in a 500 mL infusion solution bag is used as the living organism-applicable fluid. A 2 L polypropylene container is used as the hydrogen storage container. Once this container is filled with 1.2 mg/L DH concentration hydrogen water, the infusion solution bag with normal saline solution is immersed therein, an upper lid of the container is closed, and then left as is. The hydrogen water is exchanged for new water with the same DH concentration every hour. After 5 hours have elapsed, the infusion solution bag is removed from the hydrogen storage container and opened, and DH concentration and electric conductivity (EC) of the normal saline solution are measured. At this time, the DH concentration of the hydrogen water is also measured. Details of a producing apparatus for the living organism-applicable hydrogen-contained fluid are given later.

DH concentration of the normal saline solution is 0.6 mg/L, and EC is 1.2 S/m.

DH concentration of the hydrogen water is 1.2 mg/L.

Working Example 2

Commercially available normal saline solution ('Japanese Pharmacopoeia normal saline solution, Otsuka normal saline' produced by Otsuka Pharmaceutical Co., Ltd.) in a 500 mL infusion solution bag is used as the living organism-applicable fluid. A 2 L polypropylene container is used as the hydrogen storage container. The infusion solution bag with normal saline solution is placed in the container, a tube is inserted through a container opening for gas supply, and hydrogen gas is passed through at a flow rate of 100 mL/min. After 5 hours have elapsed, the infusion solution bag is removed from the hydrogen storage container and opened, and DH concentration of the normal saline solution is measured.

DH concentration of the normal saline solution is 0.46 mg/L.

Working Example 3

Commercially available normal saline solution ('Japanese Pharmacopoeia normal saline solution, Otsuka normal saline' produced by Otsuka Pharmaceutical Co., Ltd.) in a 500 mL infusion solution bag is used as the living organism-applicable fluid. A 2 L polypropylene container is used as the hydrogen storage container. Once this container is filled with 0.9 mg/L DH concentration hydrogen water, the infusion solution bag with normal saline solution is immersed therein, an upper lid of the container is closed, and then left as is. After 1 hour has elapsed, the infusion solution bag is removed from the hydrogen storage container and opened, and DH concentration of the normal saline solution is measured.

DH concentration of the normal saline solution is 0.18 mg/L.

Working Example 4

Commercially available normal saline solution ('Japanese Pharmacopoeia normal saline solution, Otsuka normal saline' produced by Otsuka Pharmaceutical Co., Ltd.) in a 500 mL infusion solution bag is used as the living organism-applicable fluid. A 10 L polypropylene container connected to an electrolyzed water generating device is used as the hydrogen storage container.

Note that this electrolyzed water generating device is the electrolytic cell and the electrolyzed water generating device that have already been filed and disclosed in Domestic Re-publication of PCT International Application WO9910286, the entire contents of which are incorporated by reference herein. Namely, it is the electrolytic cell and the electrolyzed water generating device that include an electrolysis chamber to which raw water is fed and at least one pair of electrode plates respectively provided inside and outside of the electrolytic chamber sandwiching a membrane therebetween; wherein the electrode plate outside of the electrolysis chamber is provided in contact with the membrane or leaving a slight gap therebetween; it further includes a power supply circuit, which applies a voltage between electrode plates: cathode provided in the electrolytic chamber and anode provided outside of the electrolysis chamber. General pictures of the electrolyzed water generating device are shown in FIG. 2 (hydrogen storage container separated type) and FIGS. 3 and 4 (hydrogen storage container integrated type).

As shown in FIG. 2, water circulates while being intermittently electrolyzed within an electrolyzed water generating device 2d and the polypropylene container (hydrogen storage container) 2g, which are connected via hoses extending from a water inlet and outlet of the electrolyzed water generating device 2d, whereby the water in the container 2g is kept at a stable saturation DH concentration (1.5 to 1.6 ppm at 20 C degrees under 1 barometric pressure).

An infusion solution bag with normal saline solution is immersed in hydrogen water within the container 2g, the top lid of the container is closed, and it is left as is. After 5 hours have elapsed, the infusion solution bag is removed from the container and opened, and DH concentration, dissolved oxygen (DO) concentration, oxidation-reduction potential (ORP), and electric conductivity (EC) of the normal saline solution are measured.

DH concentration of the normal saline solution is 0.8 mg/L, DO concentration is 4.6 mg/L, ORP is −370 mV, and EC is 1.6 S/m.

In the above Working Examples 1 to 4, a single living organism-applicable fluid is placed or immersed in the hydrogen storage container; however, assuming actual use at a medical site, it is desirable that multiple living organism-applicable fluids are collectively placed or immersed in a single hydrogen storage container. However, a state of too many living organism-applicable fluids being squeezed into a single hydrogen storage container is undesirable for supplying a sufficient amount of hydrogen for each of the living organism-applicable fluids. Capacity of the hydrogen storage container is preferably the same or greater than the total capacity of living organism-applicable fluids placed or immersed therein, more preferably two times or greater, even further preferably four times or greater.

Working Example 5

One commercially available normal saline solution ('Japanese Pharmacopoeia normal saline solution, Otsuka normal saline' produced by Otsuka Pharmaceutical Co., Ltd.) in a 500 mL infusion solution bag, and two of commercially available normal saline solution ('Japanese Pharmacopoeia normal saline solution, normal saline MP' produced by Mylan Inc.), each in a 100 mL infusion solution bag, a total of three solutions are used as the living organism-applicable fluid. One of the 100 mL of normal saline solution undergoes removal of air in the headspace from a bag opening using a hypodermic syringe.

A 10 L polypropylene container (see FIG. 2) connected to the same electrolyzed water generating device as in Working Example 4 is used as the hydrogen storage container. As described above, the hydrogen water in the container is kept at a DH concentration of 1.5 to 1.6 ppm. The three bags of normal saline solution are immersed in the hydrogen water, the upper lid of the container is closed, and it is left as is. After 5.5 hours have elapsed, each of the bags of saline solution are removed from the container and opened, and respective DH concentrations are measured.

DH concentration of normal saline solution (500 mL) is 0.787 mg/L.

DH concentration of normal saline solution (100 mL) is 0.34 mg/L.

DH concentration of the normal saline solution (100 mL, air-removed) is 0.810 mg/L.

While this working example includes an example of removing air from the headspace of the infusion solution bag before including hydrogen into the living organism-applicable fluid, more hydrogen than in cases where such processing is not carried out is included.

Namely, air in the headspace of the container of living organism-applicable fluid and dissolved gas (dissolved oxygen) included in the living organism-applicable fluid is considered to contribute to prevent inclusion of a given quantity or greater of hydrogen molecules into the living organism-applicable fluid. In the case of wanting to include more hydrogen molecules in the living organism-applicable fluid, removing the dissolve gas (dissolved oxygen) from the living organism-applicable fluid by removing excess air from the container of the living organism-applicable fluid is preferred.

With the present invention, it is preferable that regardless of whether the hydrogen molecules in the hydrogen storage container are supplied as a gas or as a liquid, air or dissolved gas within the container of the living organism-applicable fluid is removed through the aforementioned means or means of decompression or the like before exposing the living organism-applicable fluid to the hydrogen molecules. However, the most desirable of those is to nondestructively remove air or gas from the outside of the container by means of decompression or the like.

It is assumed that the nondestructive processing for including hydrogen in the living organism-applicable fluid according to the present invention implements a producing process (mainly a subsequent process to packaging) at a living organism-applicable fluid producing factory, and also implements it at a medical site according to fluid-administering schedule for each patient. In that case, in order to prevent hydrogen that has been included once from transmitting through the container and escaping out again, it is preferable that a person in charge of the nursing unit or the like starts the processing for including hydrogen in the living organism-applicable fluid first such that it is finished right before estimated start time of administering the fluid. In this case, it is a big merit that the person in charge of nursing can select and decide the DH concentration to be included in the living organism-applicable fluid for each patient by adjusting conditions (immersion and exposure time for living organism-applicable fluid, DH concentration and hydrogen gas mixed concentration in the hydrogen storage container, and the like) for the hydrogen-including processing.

Incidentally, it is preferable that the DH concentration of the living organism-applicable fluid reaches approximately 0.01 ppm, more preferably 0.05 ppm or greater. If the DH concentration of the living organism-applicable fluid reaches approximately 0.01 ppm, it can be considered that, for example, at the time of intravenous drip, even if a quantity of hydrogen molecules to be reduced from preparation time until intravenous drip start or in the step where the living organism-applicable fluid passes through an intravenous drip tube is subtracted, a further effective dose of hydrogen molecules is assured by the time it reaches blood vessels.

It has been confirmed by the inventor(s) that during approximately three hours from when the living organism-applicable fluid in the plastic container is immersed in hydrogen water of an almost saturation DH concentration, the living organism-applicable fluid quickly dissolves the hydrogen, reaches around 10 to 40% of the DH concentration of the living organism-applicable fluid, and thereafter, the dissolving rate of hydrogen becomes comparatively slow, gradually increasing to the DH concentration of the hydrogen water.

Moreover, from around when the DH concentration of the living organism-applicable fluid reaches approximately 60 to 90% of that of the hydrogen water after 10 hours have elapsed, the dissolving rate of hydrogen becomes even slower, and it has been confirmed that the DH concentration of the hydrogen water hardly changes even after 24 hours have elapsed.

Accordingly, this means that the DH concentration of the hydrogen water according to the present invention is preferably 50.0 ppb (0.05 ppm/1) or greater, more preferably 55.5 ppb (0.05 ppm/0.9) or greater, further preferably 62.5 ppb (0.05 ppm/0.8) or greater, even further preferably 71.4 ppb (0.05 ppm/0.7) or greater, and yet even further preferably 83.3 ppb (0.05 ppm/0.6) or greater.

Incidentally, a producing apparatus for living organism-applicable hydrogen-contained fluid can be connected as a peripheral device to an intravenous drip (fluid infusion) device or the like provided to each patient during treatment. In this case, since it is assumed that a patient moves together with the intravenous drip (fluid infusion) device within a hospital, instruments to be added to the device are preferably as small as possible, and capacity of the hydrogen storage container is basically capacity allowing accommodation of a 100 or 500 mL bag of intravenous drip (fluid infusion) solution plus a little extra. More specifically, with reference to the aforementioned electrolyzed water generating device and Domestic Re-publication of PCT International Application WO99/10286, the electrolytic cell described therein can be used as a hydrogen storage container. In Working Example 4 given above, a polypropylene container is used in addition to the electrolyzed water generating device, and the living organism-applicable fluid is immersed in a container connected to the electrolytic cell; however, in this example, since the electrolytic cell itself of the electrolyzed water generating device is used as a hydrogen storage container including a hydrogen (hydrogen water) supply function, the living organism-applicable fluid is immersed in the electrolytic cell itself (see FIG. 3 and FIG. 4).

While changing the equipment composition after the intravenous drip line is fundamentally unnecessary, the intravenous drip line itself can be immersed in a fluid including hydrogen molecules or exposed to a gas including hydrogen molecules so as to prevent reduction in the hydrogen molecules in the process where the living organism-applicable fluid passes through the intravenous drip line. Moreover, when assuming a case where living organism-applicable hydrogen-contained fluid is administered via the intravenous drip device or a type of (medical) device including a dialysis machine described later, wherein the hydrogen molecules reduce during the process where the living organism-applicable hydrogen-contained fluid reaches the living organism, it is desirable to supplement the reduced portion of the hydrogen molecules in that process using the aforementioned method by exposing to the hydrogen molecules the line (place allowing transmission of hydrogen molecules) or the like through which the living organism-applicable hydrogen-contained fluid passes.

In the case of this example, since it is also possible to administer an intravenous drip while supplying hydrogen to the living organism-applicable fluid via the electrolytic cell, there is little need to care about dissipation of hydrogen from the container into the air or reduction of hydrogen in the intravenous drip line during a time lag from the processing for including hydrogen in the living organism-applicable fluid up to actual start of administering the fluid.

Alternatively, the present invention can employ the following structure. Namely, living organism-applicable fluid put in a container (hereafter referred to as inner container) with medium or high hydrogen permeability such as a plastic bag is accommodated, inner container and all, in a portable hydrogen storage container (hereafter referred to as outer container) with a lower hydrogen permeability than the inner container, and the outer container is filled with a fluid or gas including hydrogen molecules such as hydrogen water. While the hydrogen transmits through the surface of the inner container to be included in the living organism-applicable fluid, it is blocked by the outer container, and not much disperses to the outside even during the circulation process and storage period. At the time of use, the inner container with the living organism-applicable fluid can be removed from the outer container and then used, or it can be used as is without removing the inner container by opening both the outer container and the inner container. Normally, since a plastic container such as a fluid infusion bag is light-weight, has little risk of breakage, and is advantageous to transportation and storage, yet is not provided with gas barrier property (oxygen barrier property) to prevent alteration, oxidation and deterioration of chemicals, when using a chemical that can be easily altered due to oxygen, secondary packaging is carried out using an outer packaging with a high gas barrier property. However, combined use with such an already available "bag-packed body" can also be appropriately utilized.

Alternatively, the present invention can employ the following structure. Namely, it is a hydrogen-permeable film-integrated type producing apparatus for living organism-applicable hydrogen-contained fluid constituted by a first system, which has a hydrogen storage container capable of stably maintaining the DH concentration of hydrogen-contained liquid supplied into the container from the outside or through means of providing a storage container itself, such as a hydrogen storage container connected to an electrolyzed water generating device, a hydrogen storage container with an electrolyzed water generating device as an electrolytic cell incorporated as a part thereof, or the aforementioned hydrogen storage container capable of continuously supplying hydrogen gas, is connected to a second system, which has a tank for storing living organism-applicable fluid such as intravenous drip solution, dialysis solution, blood for blood transfusion, and the like, or a pipeline allowing living organism-applicable fluid to flow through via a hydrogen-permeable film characterized by transmitting hydrogen, preferably a hydrogen-permeable film for passing only gas and not ions, and more preferably a hydrogen-permeable film for passing only hydrogen gas. The second system here is characterized by being closed while including a hydrogen-permeable film as a part of a dividing barrier between system exterior and interior. While there are cases where the hydrogen-permeable film is a part of an actual barrier as in FIG. 5 described later, or where it forms a closed system by connecting to the second system via a closed line as in FIG. 6, the case of being closed while including a hydrogen-permeable film is represented in this specification. Note that being closed in this case means that proper management that should limit influences of external physical and chemical conditions on the system is carried out. For example, a closed container for the purpose of preventing contamination of bacteria and microorganisms to the living organism-applicable fluid, a recursive line, which returns blood that has been lead to a dialyzer for removal of waste product and the like after it has accomplished its purpose to the living organism, and the like are closed. While hydrogen produced by the first system shifts to the living organism-applicable fluid of the second system via the hydrogen-permeable film if this device is used, since the first system for producing hydrogen and the second system for including hydrogen in the living organism-applicable fluid are separable systems, flexible response such as placing only the second system that requires stricter sanitary supervision in a clean room is easy to make. Moreover, a gas-exchange film integrated type electrolytic cell characterized by making a hydrogen-permeable film provided on the cathode chamber side of the anode membrane contact-type single-cell electrolysis device described in Domestic Re-publication of PCT International Application WO99/10286 as the first system, and shifting the hydrogen gas within cathode water of the first system to the living organism-applicable fluid of the second system is also available (see FIG. 5).

Figure 5:
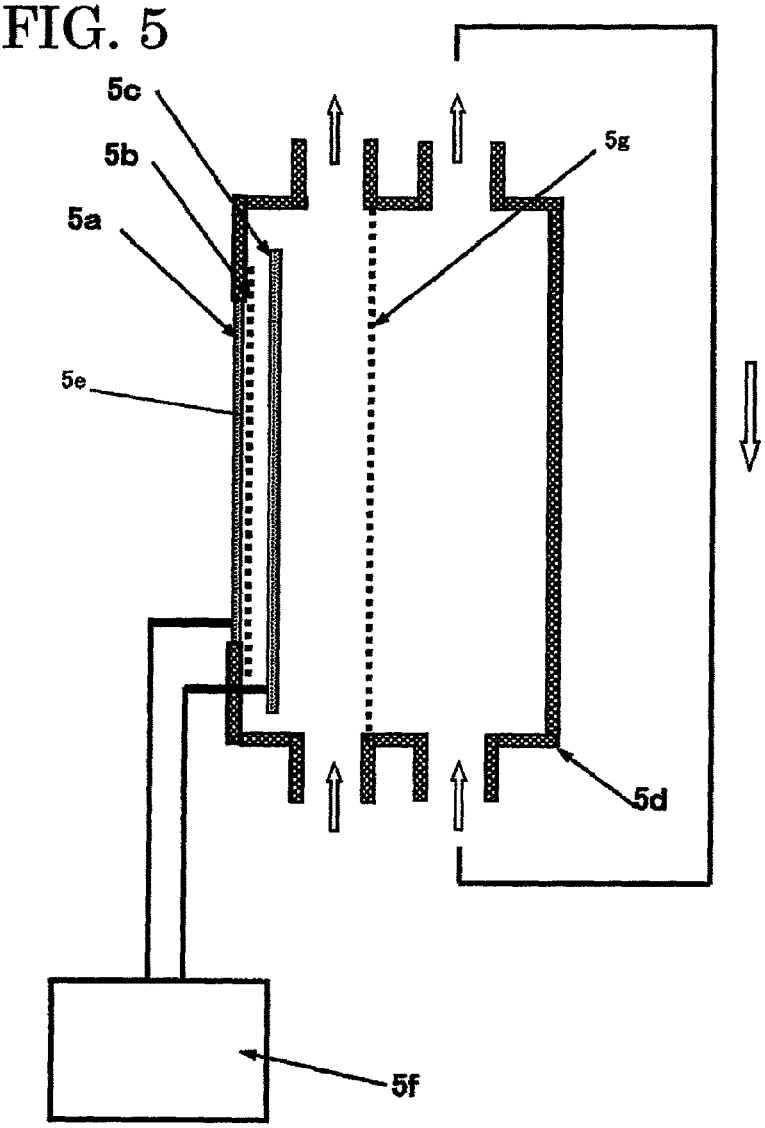
FIG. 5 is a block diagram conceptually showing a producing apparatus for a living organism-applicable hydrogen-contained fluid according to yet another embodiment of the present invention.

In FIG. 5, a gas-exchange film integrated type electrolytic cell is shown. The electrolytic cell housing 5*d* includes an anode plate 5*a*, a membrane 5*b*, a cathode plate 5*c* and gas permeable film 5*g*. An anode chamber 5*e* and a power unit 5*f* are provided. The anode chamber 5*e* is provided as tiny space between 5*a* and 5*b*.

Furthermore, the carrier for the hydrogen molecules to be supplied to the first system can be any kind of phase such as gas or liquid. Producing methods include but are not limited to mixing hydrogen gas in an appropriate concentration with another gas, bubbling hydrogen gas into water, mixing hydrogen gas into water under pressure, electrolyzing water, and generating hydrogen in water through a chemical reaction (for example, a hydrogen generating reaction between water and a metal, such as magnesium or zinc, with higher ionization tendency than hydrogen).

Further alternatively, an administering device for living organism-applicable hydrogen-contained fluid for a dialysis machine, which is characterized in that a pipeline through which living organism-applicable fluid flows in the second system is connected to a living organism, and that in the course of the living organism-applicable fluid (including biological fluid or biological water such as its own blood or own biological fluid) introduced (or tried to be introduced) from a living organism passing through the line, the living organism-applicable fluid undergoes removal of solute such as waste products as needed while it is given hydrogen via a hydrogen-permeable film from the first system, and returns (or is introduced) as living organism-applicable hydrogen-contained fluid to the living organism, is available.

Further alternatively, the following structure is available if use of the present invention for dialysis is particularly taken into consideration. Namely, in many cases, dialysis solution to be supplied to the dialysis machine for a patient is managed in an integrated manner at a dialysis facility. Namely, dialysis solution is intensively produced with exclusive equipment within a facility provided with a 'water processor' for preparing purified water (RO water) from tap water, and a 'dialysis solution feed unit' for diluting the obtained purified water with dialysis solution concentrate. As a result, when considering producing a hydrogen-contained dialysis solution, it is most effective to collectively carry out hydrogen-including processing using such water processor or dialysis solution feed unit.

However, in this case, taking into consideration an assumable problem that the hydrogen-contained dialysis solution is supplied indiscriminatingly even for dialysis solution for a patient who does not require administration of hydrogen, and an assumable problem that hydrogen leaks out in the course of the hydrogen-contained dialysis solution being supplied to the dialysis machine for each patient from a dialysis solution feed unit, a device for including hydrogen in the dialysis solution before the dialysis solution is introduced to the dialysis machine through a supply line or before it passes a dialyzer of the dialysis machine can be provided. A producing apparatus for living organism-applicable hydrogen-contained fluid using the aforementioned hydrogen-permeable film, for example, can be utilized as such device. Namely, a device characterized by shifting hydrogen from hydrogen-contained fluid with a stable DH concentration that flows through the first system to the dialysis solution (dialysis solution supplied to the dialysis machine from a supply line) that flows through the second system via a hydrogen-permeable film can be utilized as a producing apparatus for hydrogen-contained dialysis solution. Alternatively, the hydrogen-contained dialysis solution obtained by including hydrogen through the aforementioned nondestructive method can simply be poured through the supply line or the dialyzer before the dialysis machine. Thereafter, the hydrogen-contained dialysis solution flows around a semipermeable membrane such as hollow fiber within the dialyzer, and a specific amount of hydrogen is transferred into a patient's blood in a process of making concentrations of the patient's blood and content elements flowing through the film based on the principles of osmotic pressure and diffusion. Moreover, in the case of conducting peritoneal dialysis and not hemodialysis, a method of exposing to or immersing in a gas or liquid containing hydrogen molecules in a hydrogen storage container a commercially available peritoneal dialysis solution in product packaging is also possible.

Furthermore, by carrying out processing, such as coating a part or all of a semipermeable membrane, such as hollow fiber, within the dialyzer, through which the hydrogen-contained dialysis solution flows, using a hydrogen catalyst, such as platinum or palladium, antioxidative activity of hydrogen molecules can be exhibited immediately against oxidant stress in blood using the hydrogen catalyst in a process of transferring the hydrogen molecules in the dialysis solution to a patient's blood via the membrane.

Further alternatively, the present invention can employ the following structure. Namely, it is a producing apparatus for living organism-applicable hydrogen-contained fluid, as an application of the aforementioned hydrogen-permeable film-integrated type producing apparatus for living organism-applicable hydrogen-contained fluid, characterized by when transferring the hydrogen derived from the hydrogen-contained fluid produced in the first system to the living organism-applicable fluid of the second system via a hydrogen-permeable film having a hydrogen transmitting function, directly exposing the hydrogen-permeable film to the living organism. In this case, living organism-applicable fluid indicates biological fluid or biological water of a living organism itself where hydrogen is included passing through skin or a mucous membrane through exposure to the hydrogen-permeable film. More specifically, a structure of a producing apparatus for living organism-applicable hydrogen-contained fluid, which is characterized in that hydrogen (as needed, hydrogen included in an appropriate carrier such as fluid in a skin (mucous membrane) contact body, such as a belt constituted by a hydrogen-permeable film connected to the first system, or a hydrogen storage agent) deriving from the first system and transferred to the skin contact body is included in biological fluid or biological water via skin or mucous membrane by exposing the skin contact body to an appropriate region of the living organism, is available.

Merits of the case of using the present invention for living organism-applicable fluid, such as blood preparations including the aforementioned transfused pharmaceutical preparation (blood for blood transfusion), produced from a raw material of biological origin such as humans are described below. Blood preparations can generally be categorized into whole blood preparations including all blood, blood component preparations, which result from physically separating components in blood such as red blood cells, blood plasma, and blood platelets through centrifugation, and plasma derivatives, which result from physically separating and then purifying components in blood plasma, especially protein. Moreover, a preservative solution, such as blood preservative solution (Citric acid/phosphoric acid/dextrose) or red cell preservative loading solution (mannitol adenine phosphate), is often included in such blood preparations.

One of methods for including hydrogen molecules in a blood preparation other than the method of including hydrogen molecules in a preservative solution, mixing it with whole blood, blood components, blood plasma fractions, or the like, into a preparation is a method of including hydrogen molecules in a preservative solution included blood preparation. Moreover, it is preferable that hydrogen molecules are included in not only the preservative solution, but in whole blood, blood components, or blood plasma fractions as well. However, when directly including hydrogen molecules in living organism-applicable fluid, such as a blood preparation including whole blood, blood components, and/or blood plasma fractions, produced from a raw material of biological origin, it is necessary to give even more attention to contamination prevention than when including hydrogen molecules in normal saline solution or the like. From that perspective, it can be said that a producing method for living organism-applicable hydrogen-contained fluid according to the present invention, which injects hydrogen molecules from the outside of the product package, is particularly favorably used for the living organism-applicable fluid, such as a blood preparation, produced from a raw material of biological origin. Furthermore, since it is easy to accept merits of the present invention, it can be said that a producing method for the living organism-applicable hydrogen-contained fluid according to the present invention can be particularly suitable for use of a living organism-applicable fluid with a percentage of the raw material of biological origin that occupies the preparation: 10 vol % or greater, preferably 50 vol % or greater, more preferably 80 vol % or greater, or 5 wt % or greater, preferably 45 wt % or greater, or more preferably 75 wt % or greater.

Alternatively, aside from such hydrogen-contained blood preparation being produced for the purpose of medicinal benefits from hydrogen molecules including oxidant stress inhibition during blood transfusion to a living organism, it can also be produced for the purpose of controlling side effects involved in extension of expiry date of a blood preparation due to physical and chemical effects of hydrogen molecules, enhancement of activity, and blood transfusion. Moreover, from a perspective of preventing hydrogen from escaping the container and stably maintaining a high dissolved hydrogen concentration, it is preferable to continue exposing the living organism-applicable hydrogen-contained fluid to which hydrogen molecules have once been included up to a saturated concentration to hydrogen from the outside of the container.

Additional working examples are described below.

Working Example 6

Commercially available normal saline solution ('Japanese Pharmacopoeia normal saline solution, Otsuka normal saline' produced by Otsuka Pharmaceutical Co., Ltd.) in a 500 mL infusion solution bag is used as the living organism-applicable fluid. A 1.5 L cleaning filter housing is used as the hydrogen storage container. The infusion solution bag with normal saline solution is placed in the hydrogen storage container, a tube is inserted through a container opening for gas supply, and 100% hydrogen gas is passed through at a flow rate of 100 mL/min. After 5 hour has elapsed, the infusion solution bag is removed from the hydrogen storage container and opened, and DH concentration of the normal saline solution is measured.

DH concentration of the normal saline solution is 0.85 mg/L.

Working Example 7

Commercially available normal saline solution ('Japanese Pharmacopoeia normal saline solution, Otsuka normal saline' produced by Otsuka Pharmaceutical Co., Ltd.) in a 500 mL infusion solution bag is used as the living organism-applicable fluid. A 1.5 L cleaning filter housing is used as the hydrogen storage container. The infusion solution bag with normal saline solution is placed in the hydrogen storage container, a tube is inserted through a container opening for gas supply, and 100% hydrogen gas is passed through at a flow rate of 100 mL/min. After 15 hour has elapsed, the infusion solution bag is removed from the hydrogen storage container and opened, and DH concentration of the normal saline solution is measured.

DH concentration of the normal saline solution is 1.18 mg/L.

Working Example 8

Commercially available normal saline solution ('Japanese Pharmacopoeia normal saline solution, Otsuka normal saline' produced by Otsuka Pharmaceutical Co., Ltd.) in a 500 mL infusion solution bag is used as the living organism-applicable fluid. A 1.5 L cleaning filter housing is used as the hydrogen storage container. The infusion solution bag with normal saline solution is placed in the hydrogen storage container, a tube is inserted through a container opening for gas supply, and 100% hydrogen gas is passed through at a flow rate of 50 mL/min. After 15 hour has elapsed, the infusion solution bag is removed from the hydrogen storage container and opened, and DH concentration of the normal saline solution is measured.

DH concentration of the normal saline solution is 0.59 mg/L.

[Examination of Additional Working Examples]

Hydrogen molecules in the living organism-applicable fluid in a 500 mL plastic container kept in a hydrogen storage container with a 100% hydrogen gas concentration under normal temperature and pressure is dissolved over time. For example, the DH concentration of the living organism-applicable fluid, which was 0 ppm right after measurement began, is approximately 0.85 ppm (Working Example 6) after 5 hours have elapsed, and approximately 1.18 ppm after 15 hours have elapsed (Working Example 7). Meanwhile, when the hydrogen gas concentration in the hydrogen storage container is 50% (half of 100%), even after the same 15 hours have elapsed, the DH concentration of the living organism-applicable fluid is 0.59 ppm, which is half of that in Working Example 7.

As such, since the dissolved quantity of hydrogen molecules into the living organism-applicable fluid is proportional to the hydrogen gas partial pressure within the ambient gas, if the ambient gas is 100% hydrogen (partial pressure 760 mmHG) in an ultimate state of equilibrium at 20 C degrees under 1 barometric pressure, the DH concentration of the living organism-applicable fluid comes to equilibrium at 1.6 ppm (saturated hydrogen concentration), and if the ambient gas is 3.125% hydrogen (partial pressure 23.75 mmHG), the DH concentration of the living organism-applicable fluid comes to equilibrium at 0.05 ppm (saturated hydrogen concentration). Meanwhile, since a long time is needed until the ambient hydrogen gas transfers into the living organism-applicable fluid and reaches a state of equilibrium, it is preferable that the hydrogen gas has a concentration (partial pressure) no less than concentration (partial pressure) that maintains a predetermined DH concentration and the state of equilibrium in order to guide the living organism-applicable fluid to the predetermined DH concentration. Namely, it is preferable that the ambient gas is 3.125% hydrogen (partial pressure 23.75 mmHG) or greater in order for the living organism-applicable fluid to have a DH concentration of 0.05 ppm. Moreover, in order to obtain a living organism-applicable fluid with a higher DH concentration, it is preferable that the ambient gas is 0.625% hydrogen (partial pressure 4.75 mmHG) or greater, further preferably 3.125% (partial pressure 23.75 mmHG), yet even further preferably 6.25% (partial pressure 47.5 mmHG), yet even further preferably 25% (partial pressure 190 mmHG), yet even further preferably 50% (partial pressure 380 mmHG), yet even further preferably 75% (partial pressure 570 mmHG), and yet even further preferably 100% (partial pressure 760 mmHG).

Furthermore, when the hydrogen storage container is a closed container, dissolved gas other than hydrogen that has been pushed out from the living organism-applicable fluid container while the hydrogen gas is dissolved into the living organism-applicable fluid is displaced by the ambient gas in the closed container, and thus the ambient gas cannot be kept at 100% hydrogen. Accordingly, in order to keep the hydrogen within the ambient gas at a high concentration, it is preferable to use a hydrogen storage container having a structure allowing emission of a part of the ambient gas from the hydrogen storage container with little explosion risk, and continuous supplying of new hydrogen gas.

While methods of supplying hydrogen gas into the hydrogen storage container are generally categorized into method using a hydrogen gas tank, method using hydrogen gas generated through electrolysis, method using hydrogen gas generated through a chemical reaction, and similar methods, an embodiment regarding the method using hydrogen gas generated through electrolysis is exemplified here.

Figure 6:
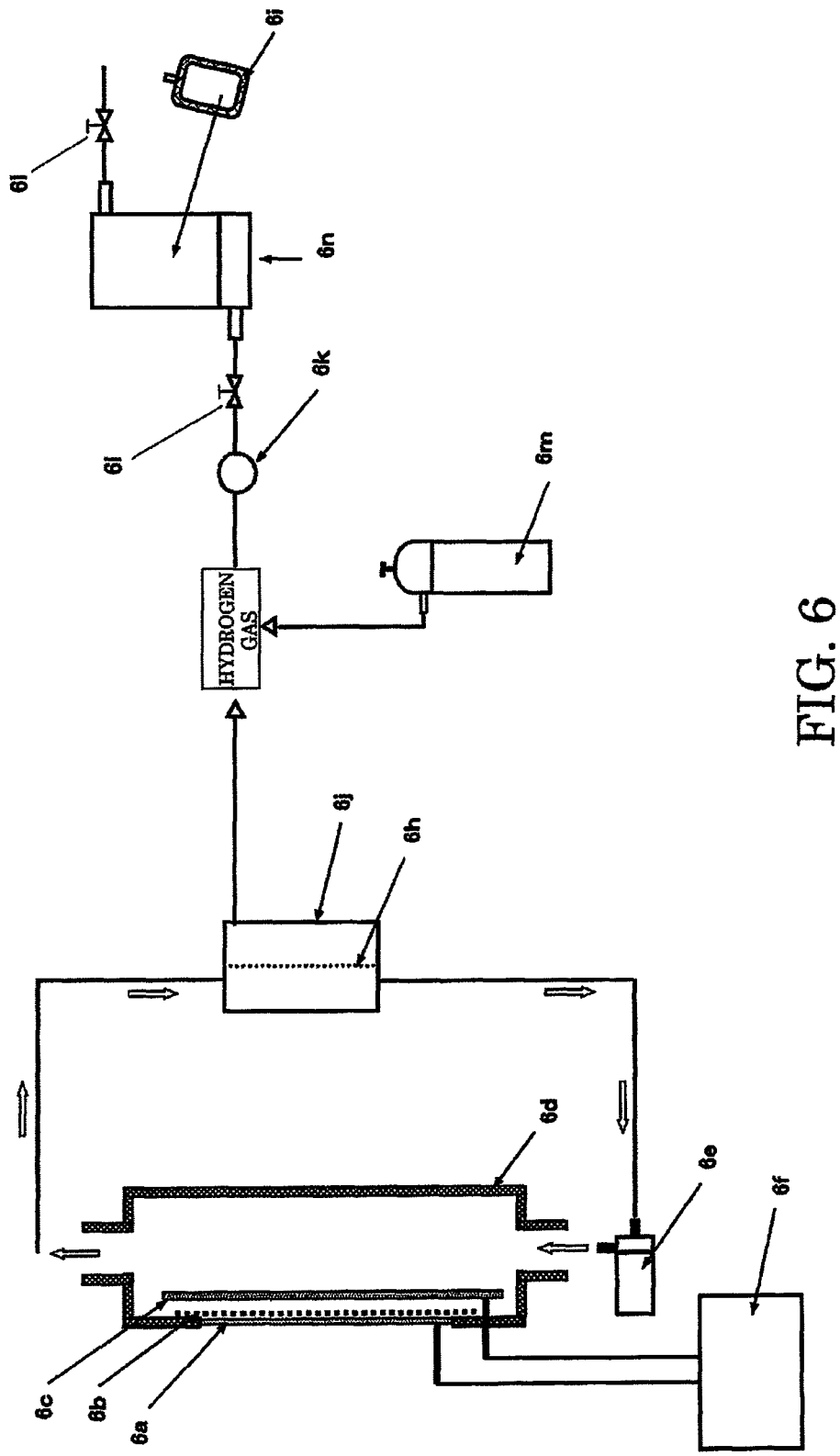
FIG. 6 is a block diagram conceptually showing a producing apparatus for a living organism-applicable hydrogen-contained fluid according to yet another embodiment of the present invention.
Figure 7:
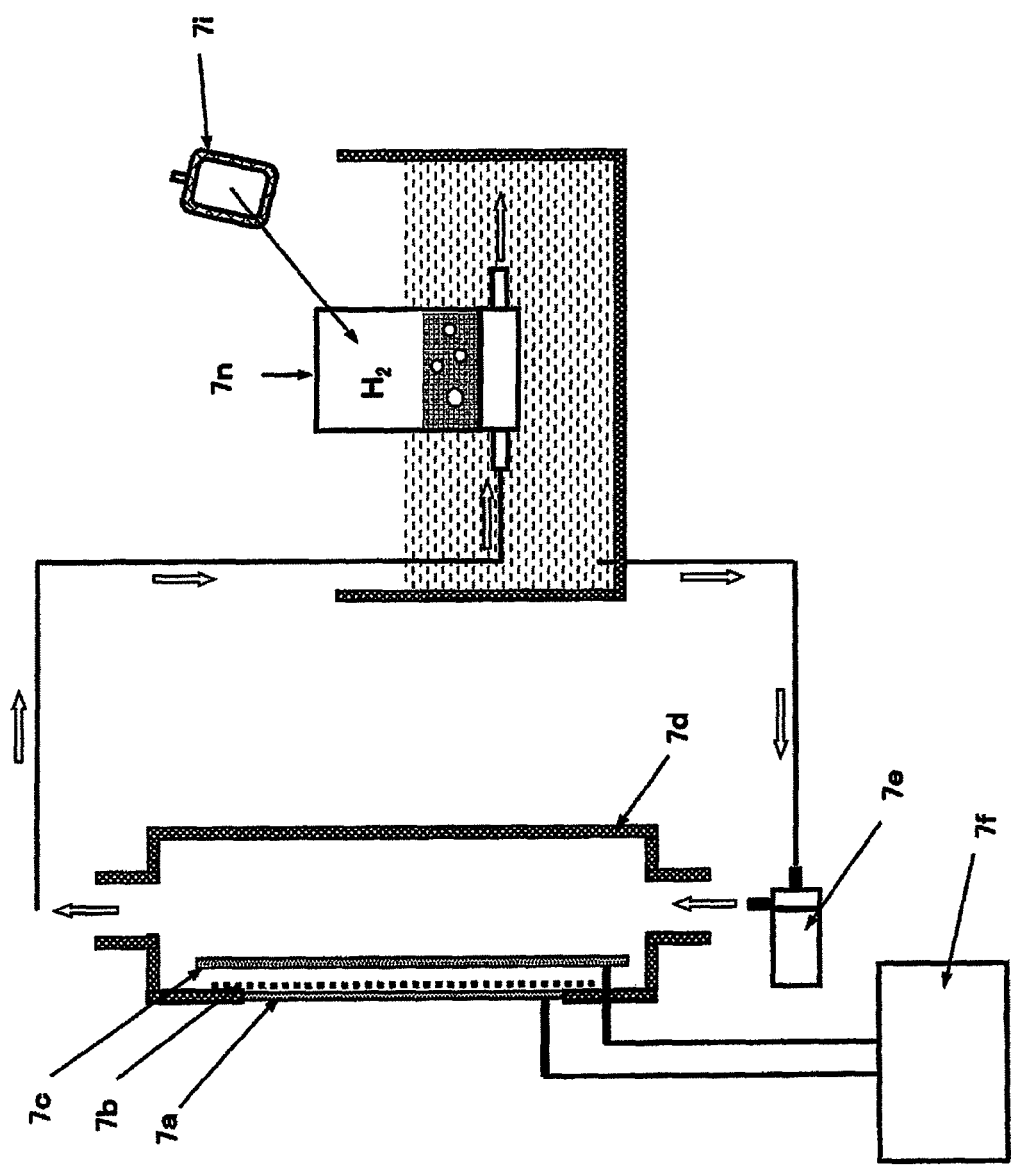
FIG. 7 is a block diagram conceptually showing a producing apparatus for a living organism-applicable hydrogen-contained fluid according to yet another embodiment of the present invention.

As shown in FIG. 6, living organism-applicable hydrogen-contained fluid can be produced by passing hydrogen water generated by an anode membrane contact-type, single-cell electrolysis device (electrolytic cell housing) $6d$ described in Domestic Re-publication of PCT International Application WO99/10286 through a gas-liquid separating device $6j$, which has a hydrogen-permeable film $6h$, and supplying the separated hydrogen gas to a hydrogen storage container $6n$, which has an arbitrary living organism-applicable fluid bag $6i$. The electrolytic cell housing $6d$ has an anode plate $6a$, a cation-exchange membrane $6b$ and a cathode plate $6c$. A power unit $6f$ is connected to the anode plate $6a$ and the cathode plate $6c$. Circulation plate $6e$ is upstream from the electrolytic cell housing $6d$. A tension adjustment device $6k$, flow control valve $6l$ and hydrogen gas tank $6m$ are also provided. As another example, as shown in FIG. 7, by supplying hydrogen water generated by an anode membrane contact-type, single-cell electrolysis device (electrolytic cell housing) $7d$ to a hydrogen storage container $7n$ or another container, and collecting hydrogen gas in an appropriate container (preferably a container with low hydrogen permeability) according to a water replacement method, hydrogen molecules can be included in an arbitrary living organism-applicable fluid placed in the container. Namely, by combining the anode membrane contact-type, single-cell electrolysis device and the water replacement method, living organism-applicable hydrogen-contained fluid can be relatively easily produced without needing a gas-liquid separating device or a tension adjustment device. The electrolytic cell housing 7d of FIG. 7 has an anode plate 7a, a cation-exchange member 7b and a cathode plate 7c. A power unit 7F is connected to the anode plate 7a and the cathode plate 7c. A circulation pump 7e is also provided upstream of the electrolytic cell housing 7d. An intravenous drip bag 7i is used.

Additional working examples are described below.

Working Example 9

Normal saline solution completely filling up a 500 mL polyethylene terephthalate container is used as the living organism-applicable fluid. A 10 L polypropylene container (see FIG. 2) connected to the same electrolyzed water generating device as in Working Example 4 is used as the hydrogen storage container. As described above, the hydrogen water in the container is stably kept at an approximately saturated concentration (1.6 ppm at 20 C degrees under 1 barometric pressure). The normal saline solution is immersed in the hydrogen water, the upper lid of the container is closed, and it is left as is. After 5 hours have elapsed, the saline solution is removed from the container and opened, and DH concentration thereof is measured.

DH concentration of the normal saline solution is 0.152 mg/L.

Working Example 10

Normal saline solution completely filling up a 500 mL polyethylene terephthalate container that is slightly thicker than that of Working Example 9 is used as the living organism-applicable fluid. A 10 L polypropylene container (see FIG. 2) connected to the same electrolyzed water generating device as in Working Example 4 is used as the hydrogen storage container. As described above, the hydrogen water in the container is stably kept at an approximately saturated concentration (1.6 ppm at 20 C degrees under 1 barometric pressure). The normal saline solution is immersed in the hydrogen water, the upper lid of the container is closed, and it is left as is. After 5 hours have elapsed, the saline solution is removed from the container and opened, and DH concentration thereof is measured.

DH concentration of the normal saline solution is 0.115 mg/L.

Working Example 11

Normal saline solution completely filling up a 500 mL aluminum laminated container is used as the living organism-applicable fluid. A 10 L polypropylene container (see FIG. 2) connected to the same electrolyzed water generating device as in Working Example 4 is used as the hydrogen storage container. As described above, the hydrogen water in the container is stably kept at an approximately saturated concentration (1.6 ppm at 20 C degrees under 1 barometric pressure). The normal saline solution is immersed in the hydrogen water, the upper lid of the container is closed, and it is left as is. After 5 hours have elapsed, the saline solution is removed from the container and opened, and DH concentration thereof is measured.

DH concentration of the normal saline solution is 0.006 mg/L.

Working Example 12

Normal saline solution completely filling up a 500 mL aluminum laminated container is used as the living organism-applicable fluid. A 10 L polypropylene container (see FIG. 2) connected to the same electrolyzed water generating device as in Working Example 4 is used as the hydrogen storage container. As described above, the hydrogen water in the container is stably kept at an approximately saturated concentration (1.6 ppm at 20 C degrees under 1 barometric pressure). The normal saline solution is immersed in the hydrogen water, the upper lid of the container is closed, and it is left as is. After 20 hours have elapsed, the saline solution is removed from the container and opened, and DH concentration thereof is measured.

DH concentration of the normal saline solution is 0.016 mg/L.

Working Example 13

Canine venous blood drawn into a 200 mL polyvinyl chloride container 'Terumo blood bag CPD' (manufactured by Terumo Corporation) containing 20 ml of blood preservative solution C (components (w/v %): sodium citrate hydrate 2.63, citric acid hydrate 0.327, glucose 2.32, and sodium dihydrogen phosphate 0.251) is used as the living organism-applicable fluid. A 10 L polypropylene container (see FIG. 2) connected to the same electrolyzed water generating device as in Working Example 4 is used as the hydrogen storage container. As described above, the hydrogen water in the container is stably kept at an approximately saturated concentration (1.6 ppm at 20 C degrees under 1 barometric pressure). The blood bag is immersed in the hydrogen water, the upper lid of the container is closed, and it is left as is. After 5 hours have elapsed, the blood bag is removed from the container and opened, and DH concentration thereof is measured using a Unisense-manufactured dissolved hydrogen measuring device (which includes H2-N (Hydrogen Needle Sensor), PA2000 (2-Channel Picoammeter).

DH concentration of the blood is 0.85 mg/L.

Working Example 14

Canine venous blood drawn into a 200 mL polyvinyl chloride container 'Terumo blood bag CPD' containing 28 ml of the aforementioned blood preservative solution C is used as the living organism-applicable fluid. A 1.5 L cleaning filter housing is used as the hydrogen storage container. The blood bag is placed in the hydrogen storage container, a tube is inserted through a container opening for gas supply, and 100% hydrogen gas is passed through at a flow rate of 100 mL/min. under a pressure of 0.01 MPa. After 5 hours have elapsed, the blood bag is removed from the hydrogen storage container and opened, and DH concentration of the blood is measured using a Unisense-manufactured dissolved hydrogen measuring device (which includes H2-N (Hydrogen Needle Sensor), PA2000 (2-Channel Picoammeter).

DH concentration of the blood is 0.87 mg/L.

A free radical elimination reaction for a hydrogen-contained blood preparation is easily measured below using diphenylpicrylhydrazyl (DPPH) or free radical reagent.

Working Example 15

Hydrogen molecules are included in the aforementioned blood preservative solution C in a polyvinyl chloride container from the outside of the container using the device described in Working Example 4, thereby obtaining hydrogen-contained blood preservative solution C of DH concentration 1.0 ppm. Next, 5 µg of platinum colloid (0.1 g of 0.05 wt % platinum colloid solution is used) is added as a catalyst to 20 cc of hydrogen-contained blood preparation model solution, which is obtained by diluting canine venous blood 1000 times with this hydrogen-contained blood preservative solution C liquid, drops of approximately 0.02 g of 0.625 wt % DDPH ethanol solution (DPPH 0.25 g/ethanol 40 g) are added, and color change thereof is examined.

The hydrogen-contained blood preparation model solution has changed seven purple-colored DPPH drops to an amber color. Namely, DPPH corresponding to 875 µg has been eliminated.

With the hydrogen-contained blood preparation model solution diluted 1000 times, red color deriving from the blood and amber color deriving from the DPPH mix together, and color change 8 and more drops could not be confirmed; however, color change of 8 or more drops can be confirmed by further diluting the solution.

Comparative Example 1

5 µg of platinum colloid (0.1 g of 0.0005 wt % platinum colloid solution is used) is added as a catalyst to 20 cc of hydrogen-contained blood preparation model solution, which is obtained by diluting canine venous blood 1000 times with this hydrogen-contained blood preservative solution C liquid, drops of approximately 0.02 g of 0.625 wt % DDPH ethanol solution (DPPH 0.25 g/ethanol 40 g) are added, and color change thereof is examined.

The blood preparation model solution has not changed the purple-colored DPPH drops to amber color. Namely, the DPPH has not been eliminated at all.

An embodiment of the hydrogen-contained blood preparation made of a combination of an inner container having hydrogen permeability and a portable hydrogen storage container having lower hydrogen permeability than the inner container is described forthwith.

Working Example 16

Once canine venous blood drawn into a 200 mL polyvinyl chloride container 'Terumo blood bag CPD' (manufactured by Terumo Corporation) containing 28 ml of the aforementioned blood preservative solution C is placed, container and all, in a 550 mL aluminum pouch, 1.5 ppm dissolved hydrogen water is filled into a space between the polyvinyl chloride container and the aluminum pouch, and an opening of the aluminum pouch is heat sealed and left for 24 hours. The aluminum pouch and the polyvinyl chloride container are opened and the dissolved hydrogen concentration of the blood preparation in the polyvinyl chloride container is then measured.

A Unisense-manufactured dissolved hydrogen measuring device (which includes H2-N (Hydrogen Needle Sensor), PA2000 (2-Channel Picoammeter) is used for measurement.

The dissolved hydrogen concentration of the blood preparation is 600 ppb.

Comparative Example 2

The hydrogen-contained blood preparation with a DH concentration of 0.85 mg/L when produced, which has been produced in Working Example 13, and a hydrogen-contained blood preparation of the same lot is unopened and left as it is for 24 hours. The polyvinyl chloride container is opened and the dissolved hydrogen concentration of the blood preparation in the polyvinyl chloride container is then measured.

A Unisense-manufactured dissolved hydrogen measuring device (which includes H2-N (Hydrogen Needle Sensor), PA2000 (2-Channel Picoammeter) is used for measurement.

The dissolved hydrogen concentration of the blood preparation is 0 ppb or less than a detection limit.

What is claimed is:

1. A method for producing a hydrogen containing fluid which is able to be used for a living organism comprising:
   exposing a container which is permeable to hydrogen and which contains and encloses the fluid to a volume of liquid carrier in which hydrogen is dissolved or a volume of gas carrier in which hydrogen is contained, until the dissolved hydrogen concentration in the fluid in the container is 0.01 mg/L or greater measured at a temperature of 20° C. under 1 atmosphere,
   wherein the exposing step does not include opening the container and wherein the hydrogen concentration in the enclosed fluid is achieved by diffusion of the hydrogen through the hydrogen permeable container from the liquid carrier or the gas carrier.

2. The method for producing a hydrogen containing fluid of claim 1, wherein
   the container with hydrogen molecule permeability is either a semitransparent or transparent container.

3. The method for producing a hydrogen containing fluid of claim 1, wherein
   the container with hydrogen molecule permeability is a plastic container.

4. The method for producing a hydrogen containing fluid of claim 1, wherein
   the liquid carrier is electrolyzed water.

5. The method for producing a hydrogen containing fluid of claim 1, wherein
   the exposing step is implemented until the dissolved hydrogen concentration of the fluid becomes 0.05 mg/L or greater.

6. The method for producing a hydrogen containing fluid of claim 1, wherein
   the fluid is produced from a raw material of biological origin.

7. The method for producing a hydrogen containing fluid of claim 6, wherein
   the fluid produced from a raw material of biological origin is a blood preparation.

8. A method for producing a hydrogen containing fluid which is able to be used for a living organism comprising:
   providing a container which is permeable to hydrogen and that allows a dissolved hydrogen concentration of a contained fluid which is a normal saline solution to be 0.1 ppm or greater when the container is immersed for 5 hours in a volume of water in which hydrogen is dissolved in approximately a saturated state measured at a temperature of 20° C. under 1 atmosphere and the volume of water is 20 times the volume of the container,
   exposing the container, which is hydrogen molecule permeable and which contains and encloses the fluid, to a volume of liquid carrier in which hydrogen is dissolved or a volume of gas carrier in which hydrogen is contained, until the dissolved hydrogen concentration in the fluid in the container is 0.01 mg/L or greater measured at a temperature of 20° C. under 1 atmosphere,
   wherein the exposing step does not include opening the container and wherein the hydrogen concentration in the enclosed fluid is achieved by diffusion of the hydrogen through the hydrogen permeable container from the liquid carrier or the gas carrier.

9. The method for producing a hydrogen containing fluid of claim 8, wherein
the container with hydrogen molecule permeability is either a semitransparent or transparent container.

10. The method for producing a hydrogen containing fluid of claim 8, wherein
the container with hydrogen molecule permeability is a plastic container.

11. The method for producing a hydrogen containing fluid of claim 8, wherein
the liquid carrier is electrolyzed water.

12. The method for producing a hydrogen containing fluid of claim 8, wherein
the exposing step is implemented until the dissolved hydrogen concentration of the fluid becomes 0.05 mg/L or greater.

13. The method for producing a hydrogen containing fluid of claim 8, wherein
the fluid is produced from a raw material of biological origin.

14. The method for producing a hydrogen containing fluid of claim 13, wherein
the fluid produced from the raw material of biological origin is a blood preparation.

* * * * *